United States Patent [19]

Fountain et al.

[11] Patent Number: 5,396,986
[45] Date of Patent: Mar. 14, 1995

[54] MIXING CAPSULE HAVING THREE TUBULAR MEMBERS

[75] Inventors: Richard W. Fountain, Pinckney; John W. Gillespie, Chelsea, both of Mich.

[73] Assignee: Special Metals Corporation, New Hartford, N.Y.

[21] Appl. No.: 229,851

[22] Filed: Apr. 19, 1994

Related U.S. Application Data

[63] Continuation of Ser. No. 77,144, Jun. 16, 1993, abandoned.

[51] Int. Cl.⁶ ............................................. B65D 25/08
[52] U.S. Cl. ................................... 206/219; 206/63.5
[58] Field of Search .............................. 206/63.5, 219

[56] References Cited

U.S. PATENT DOCUMENTS

| | | | |
|---|---|---|---|
| 3,344,914 | 10/1967 | Bloom et al. | 206/63.5 |
| 3,684,136 | 8/1972 | Baumann | 206/219 |
| 3,831,742 | 8/1974 | Gardella et al. | |
| 4,073,693 | 2/1978 | Janin | 206/219 |
| 4,136,775 | 1/1979 | Zaltsman | 206/219 |
| 4,167,228 | 9/1979 | Cheetham | |
| 4,294,351 | 10/1981 | Cheetham | |
| 4,450,957 | 5/1984 | Cohen | 206/63.5 |
| 4,515,267 | 5/1985 | Welsh | 206/219 |

*Primary Examiner*—Paul T. Sewell
*Assistant Examiner*—Thomas P. Hilliard
*Attorney, Agent, or Firm*—Robert F. Dropkin

[57] ABSTRACT

A mixing capsule for mixing a first material with a second material, and in particular, a capsule in which the materials are kept separated and brought together only at the time they are to be mixed. The capsule is characterized by a pierceable partition which separates the materials to be mixed, a projection for piercing the partition and two grooves and a ridge. One of the grooves cooperates with the ridge so as to maintain the projection away from the pierceable partition during storage and transport. The other groove cooperates with the ridge so as to hold the mixing capsule together and prevent leakage once the partition is pierced.

10 Claims, 2 Drawing Sheets

MIXING CAPSULE HAVING THREE TUBULAR MEMBERS

This application is a continuation of application Ser. No. 08/077,144, filed Jun. 16, 1993, now abandoned.

The present invention relates to a mixing capsule for mixing a first material with a second material, and in particular, to capsules in which the materials are kept separated and brought together only at the time they are to be mixed. A particular application of such a capsule is in the preparation of dental amalgams where a liquid component, generally mercury, is mixed with a powder component, generally silver or silver alloy powder. The amalgam formed is initially sufficiently plastic so that it can be metered into a tooth to be filled. After a certain period of time, it hardens.

The mixing capsule of the present invention is a three section capsule which is characterized by a pierceable partition which separates the materials to be mixed, a cutting means for piercing the partition and a locking means comprised of two grooves and a ridge. One of the grooves cooperates with the ridge to provide a means for maintaining the cutting means away from the pierceable partition during storage and transport. The other groove cooperates with the ridge to provide a means for holding the mixing capsule together and a means for preventing leakage once the partition means is pierced. A rim on one of the sections provides for proper placement of the partition.

A number of mixing capsules are known to those skilled in the art. These capsules include those described in the following U.S. Pat. Nos.:

3,831,742
4,136,775
4,167,228
4,294,351

None of the disclosed patents teach the three part capsule of the present invention, and in particular, the locking means.

It is accordingly an object of the present invention to provide an improved mixing capsule for mixing a first material with a second material.

The foregoing and other objects of the invention will become apparent from the following detailed description taken in connection with the accompanying drawings in which.

Figure 1:
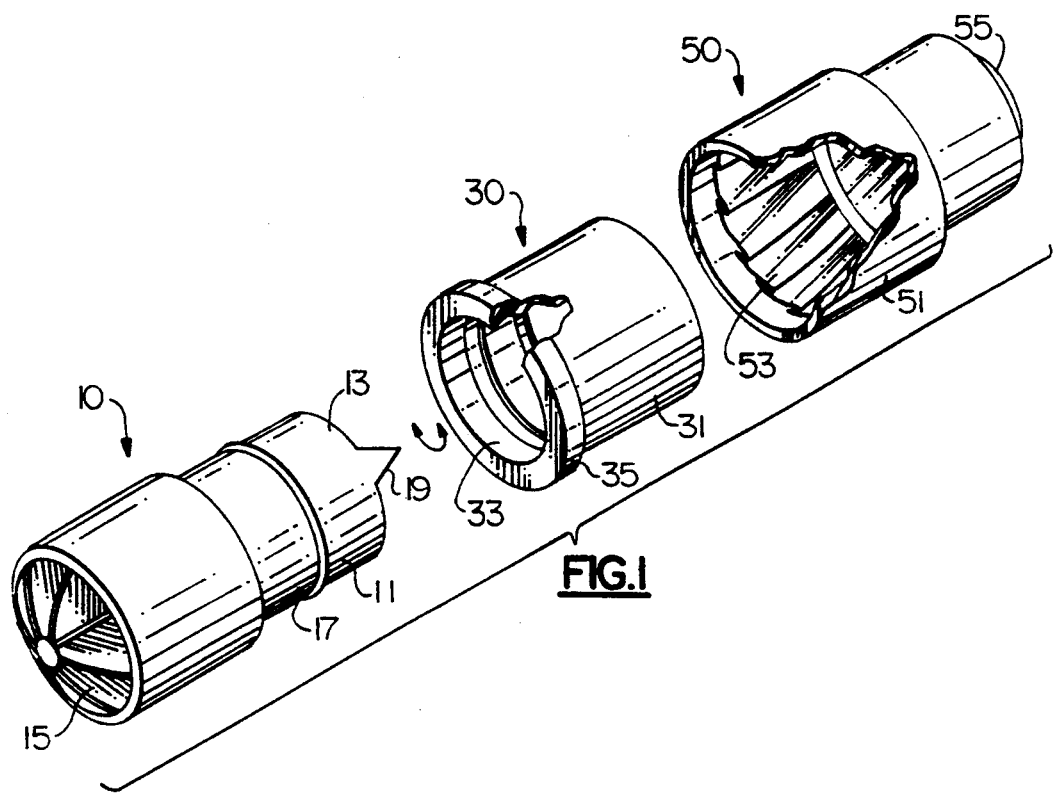
FIG. 1 is a perspective view of the three sections of the mixing capsule of the present invention.

The mixing capsule of the present invention is, in a very broad sense, comprised of three tubular members. These tubular members are most clearly shown in FIG. 1. They are identified as tubular member 10, tubular member 30 and tubular member 50.

Tubular member 30 is comprised of a tubular section 31, an open end 33, a rim 35 at its open end, a pierceable partition 37 attached to tubular section 31, a first groove 39 along its inner diameter and a second groove 41 along its inner diameter. Tubular section 31 is preferably of a substantially uniform outer diameter. Rim 35, which is present in preferred embodiments of the present invention, has an outer diameter larger than the outer diameter of tubular section 31. Groove 39 is closer to open end 33 than is groove 41. Pierceable partition 37 is preferably attached to the end of tubular section 31 that is away from rim 35. Pierceable partition 37 is typically heat sealed to tubular section 31. It can, however, be attached by other techniques well known to those skilled in the art. These techniques include ultrasonic welding and adhesives. The inner diameter of tubular section 31 is, preferably, slightly smaller at one end than at the other. It is smaller at the end that is away from rim 35 so as to produce a tighter fit with tubular section 11.

Figures 2, 3:
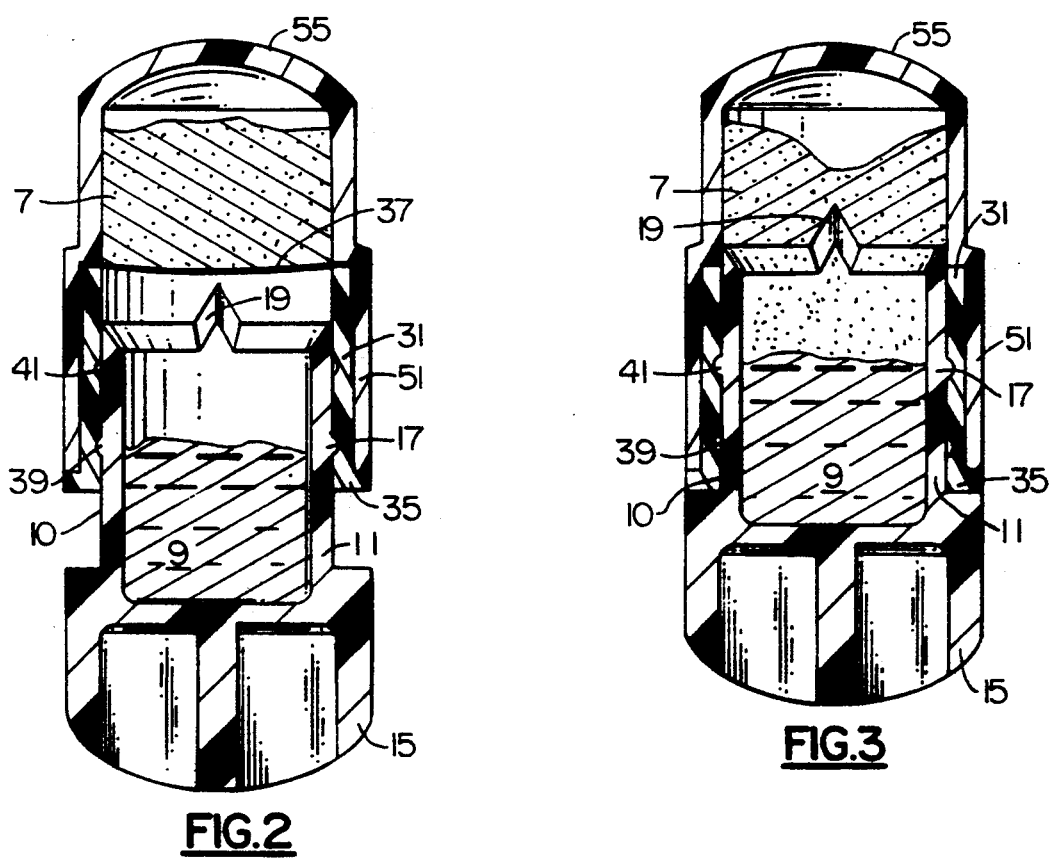
FIGS. 2 and 3 are longitudinal sectional views of the mixing capsule of the present invention showing the component parts of the mixing capsule in various positions during use of the capsule.

Tubular member 50 is comprised of a tubular section 51, an open end 53 and a closed end 55. The inner diameter of tubular section 51, which is preferably substantially uniform, is generally such as to provide a force fit with the outer diameter of tubular section 31. Tubular member 50 and tubular member 30 define between them a first chamber 7 for receiving the first material to be mixed when tubular member 30 is inserted into tubular member 50. Tubular member 50 may be fixedly joined to tubular member 30. This joining could be an ultrasonic weld along rim 35. Such a weld would provide a means for preventing leakage once pierceable partition 37 is pierced as shown in FIG. 3.

Figure 4:
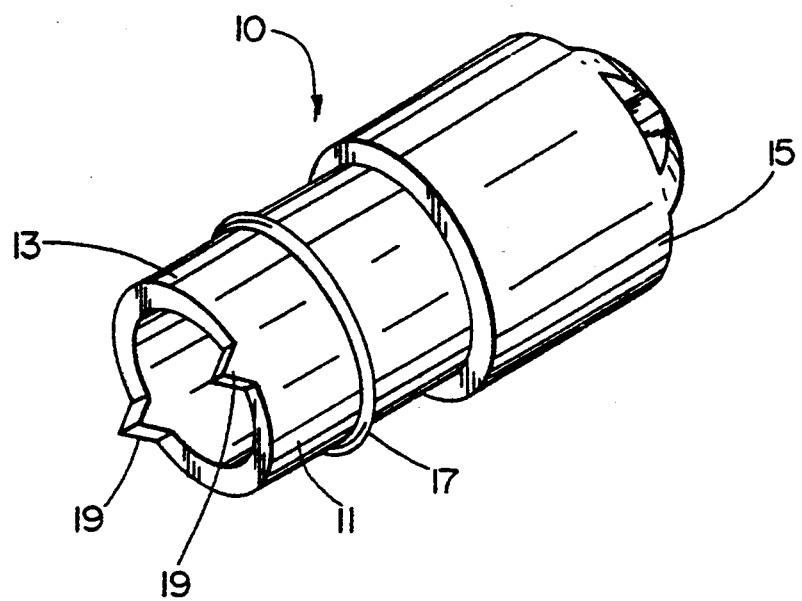
FIG. 4 is a front perspective view of one section of the mixing capsule shown in FIG. 1.
Figure 5:
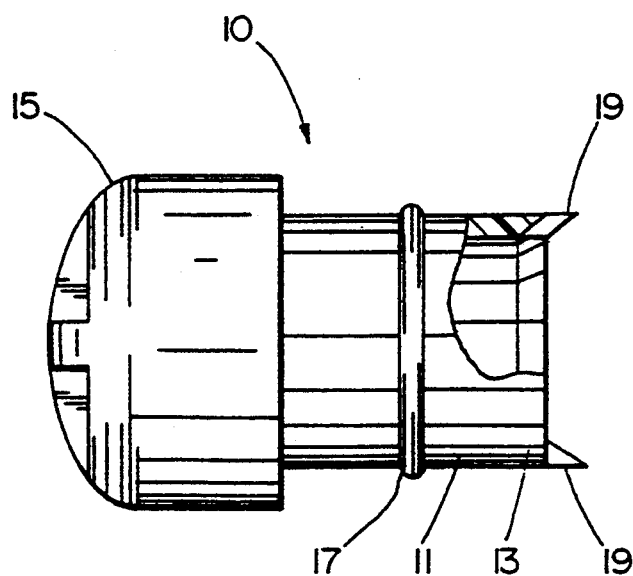
FIG. 5 is a side view of the section of the mixing capsule shown in FIG. 4.

Tubular member 10 is comprised of a tubular section 11, an open end 13, a closed end 15, a ridge 17 located on the outer diameter of tubular section 11 and cutting means 19. Tubular member 10 and tubular member 30 define between them a second chamber 9 for receiving the second material to be mixed when tubular member 10 is inserted into tubular member 30. Ridge 17 and first groove 39 provide a locking means for maintaining cutting means 19 away from pierceable partition 37 as shown in FIG. 2. Ridge 17 and second groove 41 provide a means for holding the mixing capsule together and a means for preventing leakage once pierceable partition 37 is pierced as shown in FIG. 3. Cutting means 19 is any projection capable of piercing partition 37. It is preferably two projections, one hundred and eighty degrees apart, as shown in FIGS. 4 and 5.

The mixing capsule of the present invention may be assembled by placing a first material in tubular member 50, inserting tubular member 30 into tubular member 50, placing a second material in tubular member 10 and inserting tubular member 10 into tubular member 30. Ridge 17 is brought into contact with groove 39 thereby providing a locking means for storage and transport. Tubular member 50 may be fixedly joined to tubular member 30 as discussed hereinabove.

The first and second material are brought into contact with each other by pushing tubular members 10 and 50 together and rotating them with respect to each other. Ridge 17 and groove 41 cooperate with each other and provide a means for holding the mixing capsule together and a means for preventing leakage.

It will be apparent to those skilled in the art that the novel principles of the invention disclosed herein will suggest various modifications and other applications of the same. It is accordingly desired that in construing the breadth of the appended claims that they shall not be limited to a specific embodiment of the invention as described herein.

I claim:

1. A mixing capsule for mixing a first material with a second material, comprising: a first tubular member; a second tubular member; and a third tubular member; said third tubular member being inserted in one end of said second tubular member; said second tubular member having a tubular section at the other end; said second tubular member having a pierceable partition attached to said tubular section; said first tubular member being closed at one end; said second tubular member being inserted in the other end of said first tubular member; said closed end of said first tubular member and said pierceable partition of said second tubular member defining between them a first chamber for receiving a first material to be mixed; said second tubular member having a first groove and a second groove along its inner diameter; said first groove being closer to said end of said second tubular member having said third tubular member inserted therein than is said second groove; said third tubular member having a tubular section and a ridge located thereon; said third tubular member being closed at the end opposite the end that is inserted in the second tubular member; said third tubular member having rotational cutting means at the end that is inserted in the second tubular member; said closed end of said third tubular member and said pierceable partition of said second tubular member defining between them a second chamber for receiving a second material to be mixed; said ridge and said first groove providing a locking means for maintaining said cutting means away from said pierceable partition; said ridge and said second groove providing a means for holding the mixing capsule together and a means for preventing leakage once said partition is pierced.

2. A mixing capsule according to claim 1, wherein said first tubular member is such as to provide a force fit with said tubular section of said second tubular member.

3. A mixing capsule according to claim 2, wherein said second tubular member has a rim at its end through which said third tubular member is inserted, wherein said rim has an outer diameter larger than the outer diameter of said tubular section of said second tubular member and wherein said rim abuts up against the end of said first tubular member through which said second tubular member is inserted.

4. A mixing capsule according to claim 3, wherein said pierceable partition is attached to the end of said tubular section of said second tubular member that is away from said rim.

5. A mixing capsule according to claim 1, wherein said pierceable partition is heat sealed to said second tubular member.

6. A mixing capsule according to claim 1, wherein said cutting means is at least one projection extending from the end of said third tubular member that is inserted in the second tubular member.

7. A mixing capsule according to claim 1, wherein said first and second tubular members are fixedly joined.

8. A mixing capsule according to claim 7, wherein said first and second tubular members are ultrasonically welded to each other.

9. A mixing capsule according to claim 8, wherein said first tubular member is such as to provide a force fit with said tubular section of said second tubular member.

10. A mixing capsule for mixing a first material with a second material, comprising: a first tubular member; a second tubular member; and a third tubular member; said third tubular member being inserted in one end of said second tubular member; said second tubular member having a tubular section at the other end; said second tubular member having a pierceable partition attached to said tubular section; said first tubular member being closed at one end; said second tubular member being inserted in the other end of said first tubular member; said closed end of said first tubular member and said pierceable partition of said second tubular member defining between them a first chamber for receiving a first material to be mixed; said second tubular member having a first groove and a second groove along its inner diameter; said first groove being closer to said end of said second tubular member having said third tubular member inserted therein than is said second groove; said third tubular member having a tubular section and a ridge located thereon; said third tubular member being closed at the end opposite the end that is inserted in the second tubular member; said third tubular member having a cutting means extending from the end that is inserted in the second tubular member; said cutting means being two projections, one hundred and eighty degrees apart; said closed end of said third tubular member and said pierceable partition of said second tubular member defining between them a second chamber for receiving a second material to be mixed; said ridge and said first groove providing a locking means for maintaining said cutting means away from said pierceable partition; said ridge and said second groove providing a means for holding the mixing capsule together and a means for preventing leakage once said partition is pierced.

* * * * *